United States Patent
Park

(10) Patent No.: US 7,282,111 B2
(45) Date of Patent: Oct. 16, 2007

(54) SYSTEM AND METHOD FOR MONITORING PARTICLES CONTAMINATION IN SEMICONDUCTOR MANUFACTURING FACILITIES

(75) Inventor: Bong-Jin Park, Osan-si (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 0 days.

(21) Appl. No.: 11/004,099

(22) Filed: Dec. 6, 2004

(65) Prior Publication Data

US 2005/0148188 A1    Jul. 7, 2005

(30) Foreign Application Priority Data

Jan. 2, 2004    (KR) ...................... 10-2004-0000063

(51) Int. Cl.
*H01L 21/302* (2006.01)
*C23F 1/00* (2006.01)

(52) U.S. Cl. .................... 156/345.24; 156/345.43; 118/722; 118/733

(58) Field of Classification Search ............ 216/60, 216/67; 438/7, 16, 714, 905; 156/345.24, 156/345.43; 118/722, 733
See application file for complete search history.

(56) References Cited

U.S. PATENT DOCUMENTS

| | | | | |
|---|---|---|---|---|
| 5,467,188 A | * | 11/1995 | Miyashita | 356/336 |
| 5,517,943 A | * | 5/1996 | Takahashi | 118/715 |
| 6,163,007 A | * | 12/2000 | Tanaka et al. | 219/121.48 |
| 6,825,437 B2 | * | 11/2004 | Nakano et al. | 219/121.41 |
| 2005/0173375 A1 | * | 8/2005 | Mitrovic et al. | 216/60 |

FOREIGN PATENT DOCUMENTS

| | | | |
|---|---|---|---|
| JP | 58-078428 | * | 5/1983 |
| JP | 61-240645 | * | 10/1986 |
| JP | 02-028538 | * | 1/1990 |
| JP | 04-179142 | * | 6/1992 |
| JP | 11-297629 | * | 10/1999 |
| JP | 2003-249488 | * | 9/2003 |

* cited by examiner

*Primary Examiner*—George A. Goudreau
(74) *Attorney, Agent, or Firm*—Volentine & Whitt, PLLC

(57) ABSTRACT

Provided is a particle monitoring system capable of detecting a level of polymer particle contamination on inner walls of a process chamber. Also disclosed is a method of monitoring the level of polymer particle contamination on inner walls of a process chamber.

7 Claims, 4 Drawing Sheets

FIG. 3
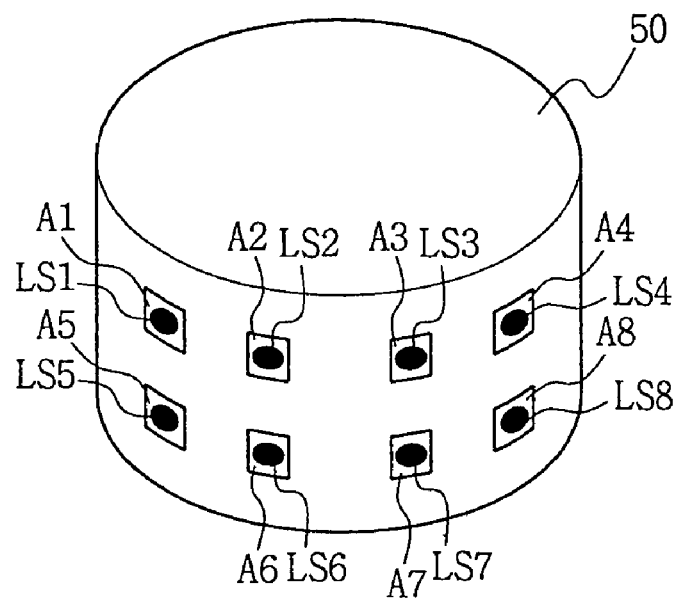
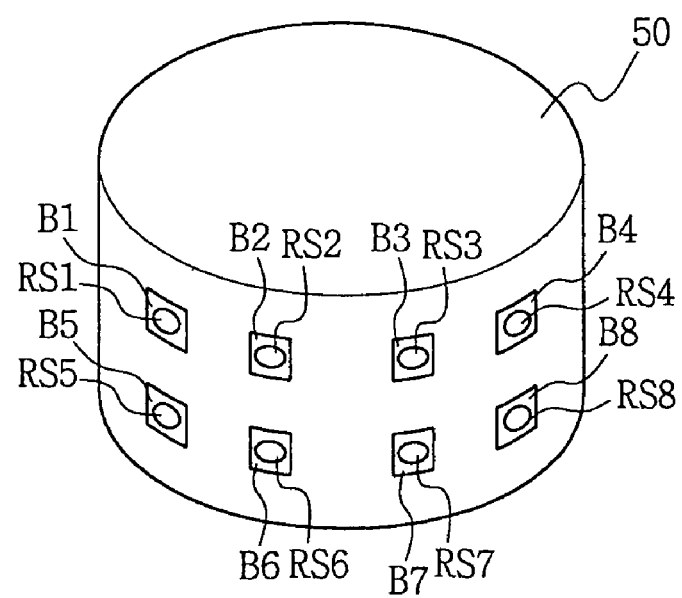

SYSTEM AND METHOD FOR MONITORING PARTICLES CONTAMINATION IN SEMICONDUCTOR MANUFACTURING FACILITIES

BACKGROUND OF THE INVENTION

1. Technical Field

The present invention generally relates to a system to monitor particle contamination in semiconductor manufacturing facilities. More particularly, the present invention generally relates to a particle monitoring system capable of automatically detecting the level of polymer deposited on inner walls of a process chamber.

A claim is made to Korean Patent Application No. 2004-63, filed on Jan. 2, 2004, the disclosure of which is hereby incorporated by reference.

2. Discussion of the Related Art

Conventional semiconductor manufacturing techniques, such as dry plasma etching, reactive ion etching, and ion milling, have developed to overcome various limitations associated with a chemical etching technique. In the dry plasma etching, the vertical etching speed is much faster than its horizontal etching speed, such that an aspect ratio can be properly adjusted. In fact, a fine feature with a high aspect ratio can be formed on a thin film having a thickness greater than 1 μm using the dry plasma etching technique.

In a process chamber under pressure, energy is added to ionize a reactive gas to thereby form plasma. Atoms having an electrical charge are attracted to a wafer having an electrical potential. The atoms collide with the wafer in a vertical direction, and areas on the wafer unprotected by a mask are removed.

The etching process is effectively implemented by utilizing a chemically reactive gas that targets a specific material. The reactive ion etching technique combines the strong etching effects of both dry plasma etching and chemical etching techniques. It is conventionally known that chemically reactive agents cause excessive electrode wear.

Preferably, plasma is uniformly distributed across the surface of a wafer to achieve a uniform etching speed over the entire surface of the wafer. For example, U.S. Pat. Nos. 4,595,484, 4,792,378, 4,820,371, and 4,960,488 generally disclose a conventional showerhead electrode to distribute gas through a plurality of holes formed on the electrode. The patents also generally disclose a gas distribution plate having a plurality of rows of apertures to provide a uniform flow of gas vapor to a semiconductor wafer.

A conventional reactive ion etching system generally includes an etching chamber having an upper electrode (anode) and a lower electrode (cathode) disposed therein. The cathode applies a negative bias to the anode and the etching chamber walls. A mask covered wafer is directly laid on the cathode. A reactive gas, such as $CF_4$, $CHF_3$, $CClF_3$, $SF_6$, or a mixture thereof is supplied together with $O_2$, $N_2$, He or Ar gas into the etching chamber. The etching chamber is maintained at a pressure of a few millitorr. The upper electrode is provided with a plurality of gas holes to uniformly distribute the gases in the etching chamber. An electric field applied between the anode and the cathode dissociates the reactive gas to form the plasma. The surface of the wafer is etched by a chemical reaction with the reactive ions, and a momentum transfer of ions colliding against the surface of the wafer. The electric field created by the electrodes attracts ions toward the cathode, such that the ions are guided to vertically collide against the surface of the wafer. Therefore, this process can produce a well-defined vertically etched side wall.

In another conventional etching process, a vacuum processing chamber is supplied with an etching gas or a deposition gas. The gas is activated into a plasma state by applying an RF field to implement etching, and then a chemical vapor deposition (CVD) process is carried out on a substrate. U.S. Pat. Nos. 4,340,462, 4,948,458, 5,200,232, and 5,820,723 generally disclose a parallel plate transformer coupled plasma (TCPTM) (referred to as inductively coupled plasma (ICP)), an electron-cyclotron reactor, and components thereof. The components preferably have high anti-corrosion properties, because the reactor must be resistant to corrosion caused by the plasma atmosphere, and contamination by particles and/or heavy metals.

Inner walls of a plasma reactor are generally made of aluminum or aluminum alloy. Several techniques for coating the inner walls with various coating materials have been proposed to prevent the corrosion of the inner walls. For example, U.S. Pat. No. 5,641,375 generally discloses an anodized aluminum chamber to reduce plasma corrosion and wear of the inner walls. However, once the anodized layer wears off, the chamber itself must be replaced.

U.S. Pat. No. 4,491,496 generally discloses a technique of flame spraying $Al_2O_3$ on a metallic surface of an etching chamber. U.S. Pat. No. 5,680,013 teaches that a ceramic coating usually cracks due to the thermal coefficient of expansion mismatch between aluminum and the ceramic coating, resulting in the deterioration of the exposed aluminum by the plasma species. U.S. Pat. No. 5,085,727 discloses a plasma chamber having a carbon coated inner wall, in which the coating is deposited by plasma assisted CVD.

U.S. Pat. Nos. 5,366,585, 5,556,501, 5,788,799, 5,798, 016, and 5,885,356 generally disclose a liner arrangement to protect an inner wall of a plasma chamber. For example, U.S. Pat. No. 5,366,585 discloses a free standing ceramic material machined from solid alumina and having a thickness of at least 0.005 inches. A ceramic layer is deposited without consuming the underlying aluminum.

U.S. Pat. No. 5,556,501 discloses a process-compatible liner made of polymer, quartz or ceramic. U.S. Pat. No. 5,788,799 discloses a temperature-controlled ceramic liner having a resistance heater. The ceramic comprises oxides of alumina, silica, titania, and zirconia; carbides such as silicon carbide, titanium carbide, and zirconium carbide; and nitrides such as aluminum nitride, boron nitride, silicon nitride and titanium nitride. U.S. Pat. No. 5,798,016 discloses a liner for an etching chamber made of ceramics, aluminum, steel and/or quartz. Aluminum is a preferred material because it is easy to machine. Preferably, the lining is coated with $Al_2O_3$, $Sc_2O_3$, or $Y_2O_3$ to protect the aluminum against the plasma. U.S. Pat. No. 5,885,356 discloses a wafer pedestal comprised of a ceramic liner of alumina and a ceramic shield of aluminum nitride. U.S. Pat. No. 5,904, 778 discloses a chamber wall, a chamber roof, or a collar around a wafer coated with a free standing silicon carbide substrate by a CVD process. U.S. Pat. No. 5,292,399 discloses a wafer pedestal enclosed with a SiC ring. U.S. Pat. No. 5,182,059 discloses a technique of producing SiC sintered material.

Various materials for use as plasma reactor components (e.g., the showerhead gas distributing system) have been proposed. For example, U.S. Pat. No. 5,569,356 discloses a showerhead made of silicon, graphite or silicon carbide. U.S. Pat. No. 5,888,957 discloses a showerhead made of amorphous silicon, SiC or Al. U.S. Pat. Nos. 5,006,220 and 5,022,979 disclose coating a showerhead electrode with SiC by a CVD process to provide a surface thereof with highly pure SiC.

However, a technique to improve the substance and/or coating used as plasma reactor components, in view of the demand for highly pure and anti-corrosive components for semiconductor processing facilities is required. In addition, it is useful for a chamber material to utilize a substance capable of extending the service life of the plasma reactor, and thus reducing the down time and process costs.

In a conventional dry etching chamber, a semiconductor wafer is etched by plasma gas and RF power. However, the wafer may be damaged by byproduct (polymer) particles during the etching process. According to the conventional method of cleaning the dry etching chamber, the etching chamber is periodically cleaned to remove the polymer particles. The polymer particles usually deposit on the inner walls of the process chamber, but due to leakages, regardless of process management (PM) schedules, a high number of particles are produced, which adversely affect process yields. In order to solve the above problem, the level of the polymer particles must be monitored, and the etching chamber cleaned accordingly. The conventional method of monitoring and identifying the level of polymer particles consumes a lot of time which lowers productivity.

SUMMARY OF THE INVENTION

Therefore, the present invention is directed to provide system to monitor particle contamination in a process chamber. The system generally comprises a process chamber, at least two transparent windows installed on opposite sides of the process chamber, a light emitting device installed on one of the at least two transparent window, a light receiving sensor installed on the other one of the at least two transparent window, and a controller to detect a level sensed by the light receiving sensor.

In a related aspect, the present invention provides a method of monitoring particle contamination in a process chamber by sending a light via a light transmitting device through at least one of a plurality of transparent windows installed in the process chamber, receiving the light in a light receiving sensor installed in another one of the plurality of transparent windows, determining a transmission value for the light, and comparing the transmission value with a set value in a controller.

BRIEF DESCRIPTION OF THE DRAWINGS

The above and other aspects of the present invention will become more apparent to those of ordinary skill in the art in view of the detailed preferred embodiments described herein and with reference to the attached drawings in which:

FIG. 3 is a schematic view depicting an assembled transparent window, light emitting sensors, and light receiving sensors according to another embodiment of the present invention.

DETAILED DESCRIPTION OF THE INVENTION

The present invention will now be described more fully hereinafter with reference to the accompanying drawings, in which preferred embodiments of the invention are shown. This invention may, however, be embodied in different forms and should not be construed as limited to the embodiments set forth herein. Rather, these embodiments are provided as teaching examples of the invention. Like numbers refer to like elements throughout the specification.

Figure 1:
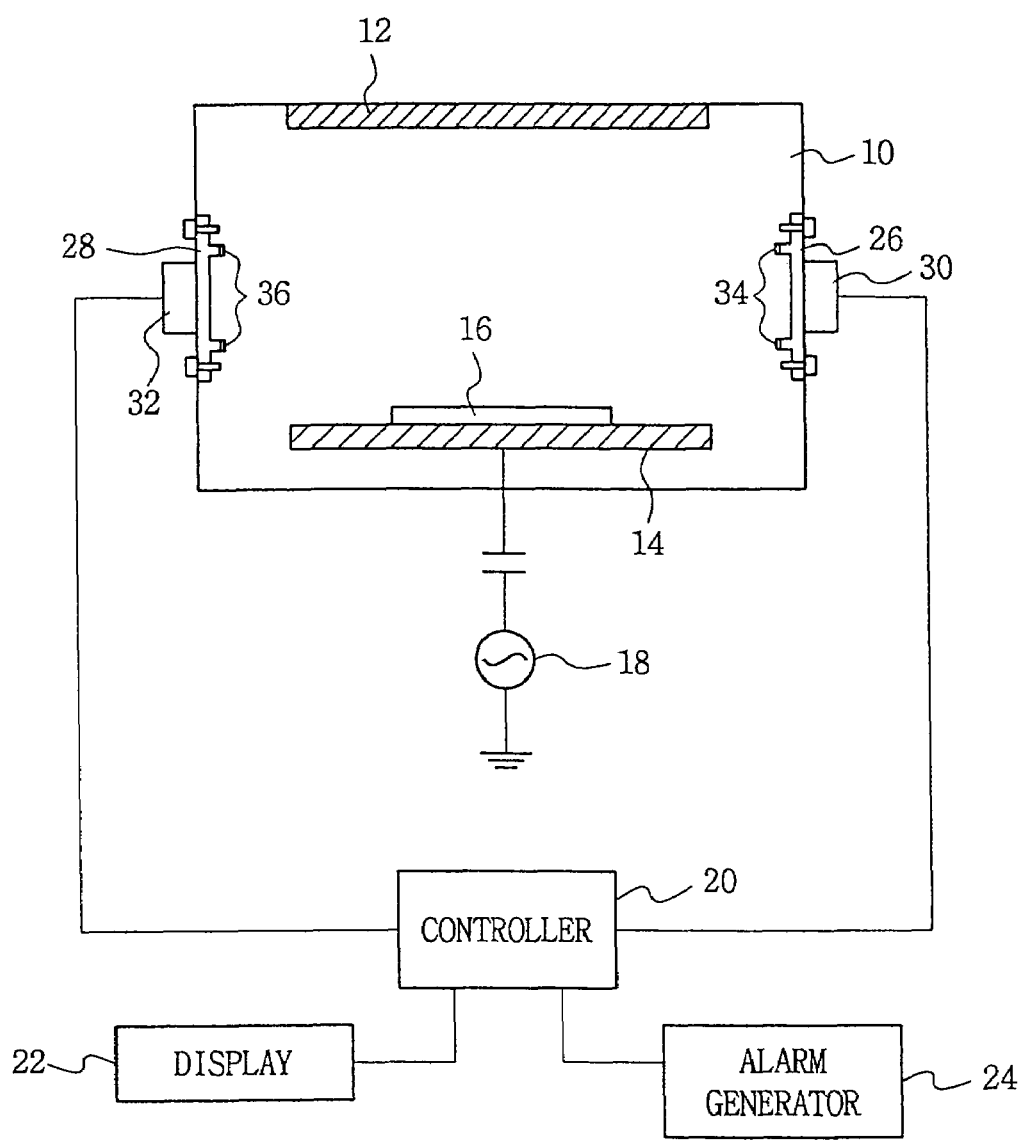
FIG. 1 is a schematic view of a system to monitor particle contamination in a semiconductor manufacturing facility according to a preferred embodiment of the present invention.

FIG. 1 is a schematic view of a system to monitor particle contamination in a semiconductor manufacturing facility according to a preferred embodiment of the present invention.

The system includes a plasma chamber 10 adapted to etch wafers; an upper electrode 12 disposed in an upper portion of plasma chamber 10 to apply a high frequency power; a lower electrode 14 disposed in a lower portion of plasma chamber 10 to apply a high frequency power and to secure a wafer 16 thereon; an RF electric power generating unit 18 to supply power to lower electrode 14; first and second transparent windows 26, 28 symmetrically installed on opposite sides of process chamber 10, wherein first and second transparent windows 26, 28 are preferably made of quartz to allow light to pass; a light emitting device 30 installed on first transparent window 26 to emit light; a light receiving sensor 32 installed on second transparent window 28 to receive the light from light emitting device 30; O-rings 34, 36 tightly fitted in internal bosses of first and second transparent windows 26, 28 to prevent gas leakage from plasma chamber 10; a controller 20 to convert the light received from light receiving sensor 32 into a detected voltage, wherein if the detected voltage is less than a set voltage, an indication is made that the inner walls of plasma chamber 10 are contaminated with polymer particles; therefore, controller 20 operates an interlock and generates an alarm; a display 22 to display the level of polymer particles deposited on the inner walls of plasma chamber 10; and an alarm generator 24 to generate an alarm indicating an unacceptable level of polymer particle deposition.

Figure 2:
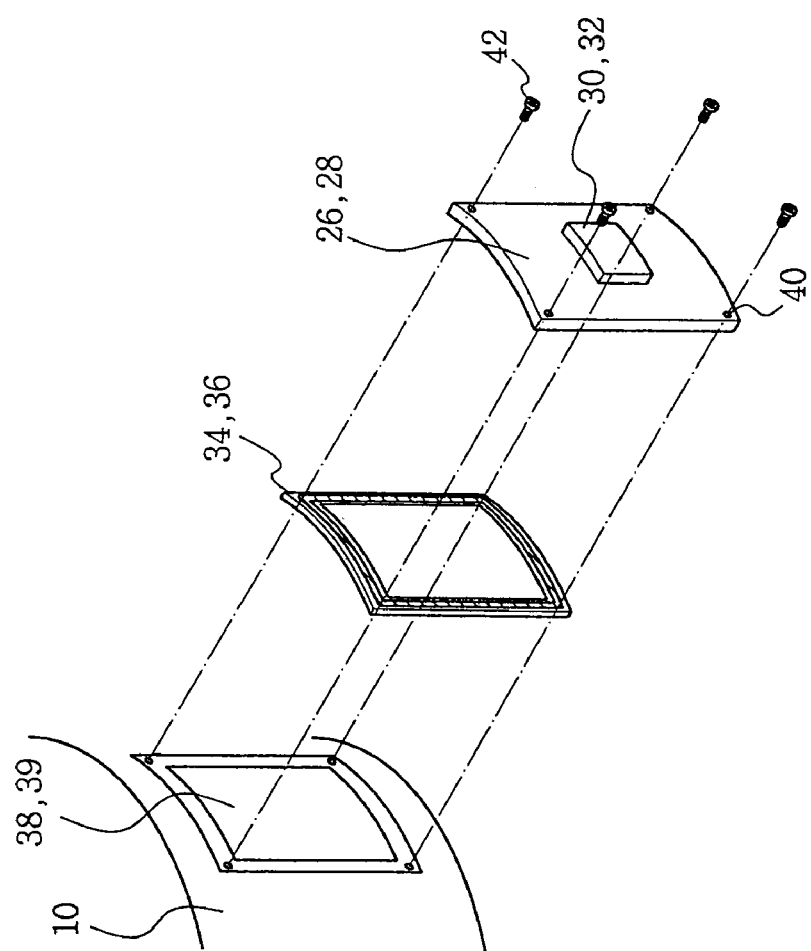
FIG. 2 is a schematic view of quartz windows of FIG. 1.

FIG. 2 is a schematic view of the quartz windows of FIG. 1.

Opposite sides of plasma chamber 10 are respectively provided with openings 38 and 39. First and second transparent windows 26, 28 are provided within the sidewalls of plasma chamber 10 with screws 42 over openings 38 and 39, respectively. Each of O-rings 34 and 36 has a groove, wherein the bosses of first and second transparent windows 26, 28 are inserted therein.

Operation of the preferred embodiment of the present invention will be explained with reference to FIGS. 1 and 2.

A wafer is loaded in plasma chamber 10, and a reaction gas is supplied to generate plasma. At this time, polymer particles begin to be deposited on the inner wall of processing chamber 10. While processing chamber 10 is prepared for a next process, controller 20 undertakes a PM operation. If the PM operation confirms it is time for a cleaning, controller 20 outputs an alert signal to at least one of display 22 and/or alarm generator 24. If it is not the time for a cleaning, controller 20 checks light emitting sensor 30 and light receiving sensor 32. Light receiving sensor 32 receives light from light emitting device 30 and generates a detected voltage in relation to the received light. If the detected voltage generated by light receiving sensor 32 exceeds the set voltage (for example, 6 V), controller 20 concludes that the level of polymer particle contamination is insufficient to warrant a cleaning. If, however, the detected voltage is less than the set voltage, controller 20 concludes that the level of polymer particle contamination on the inner walls of processing chamber 10 is such that a cleaning is required. Controller 20 accordingly operates an interlock and outputs an alert signal to display 22 and/or alarm generator 24. Accordingly, display 22 displays the interlock, and alarm generator 24 sounds an alarm.

FIG. 3 is a schematic view depicting assembled transparent windows, light emitting devices, and light receiving sensors according another preferred embodiment of the present invention.

Figure 4:
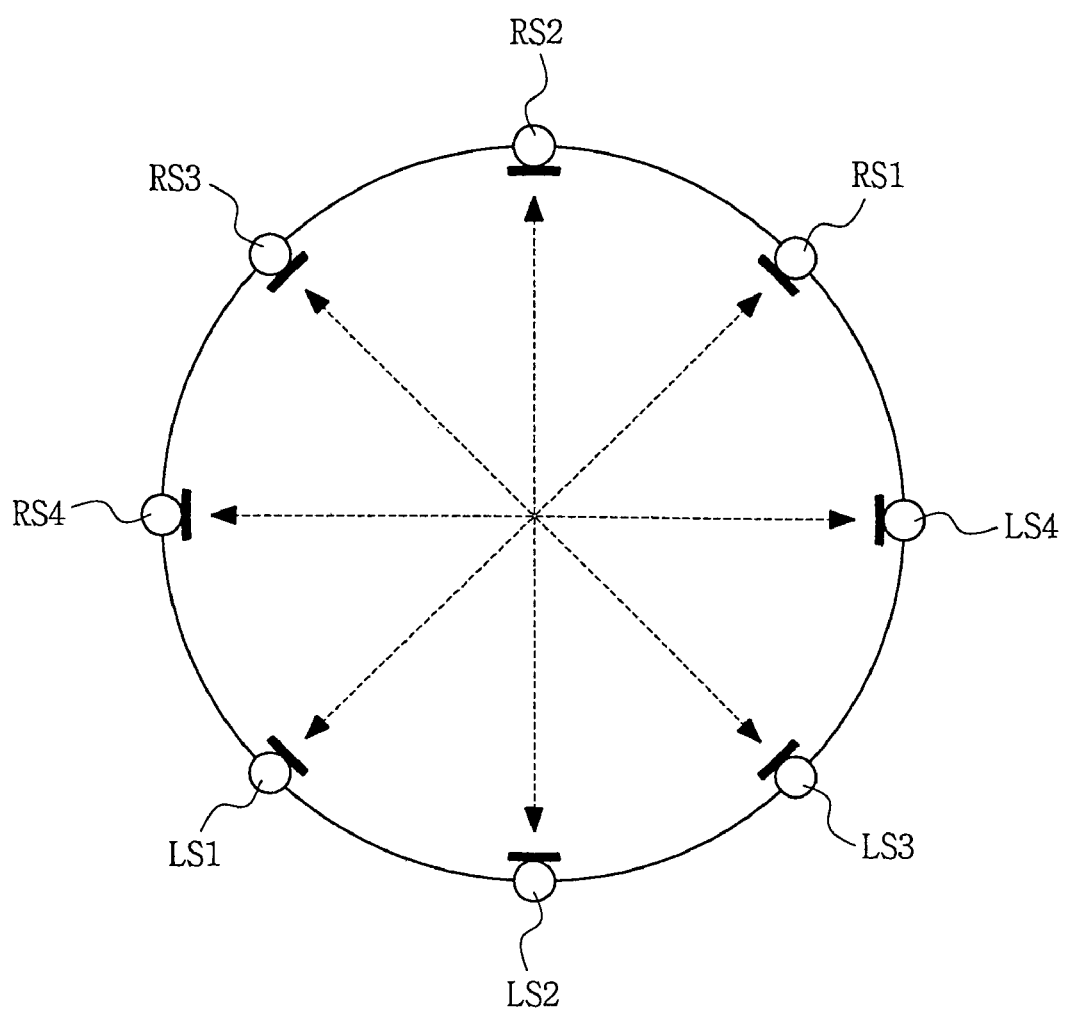
FIG. 4 is a perspective view depicting the assembled light emitting sensors and light receiving sensors of FIG. 3.

FIG. 4 is a perspective view depicting the assembled light emitting devices and light receiving sensors of FIG. 3. Four light emitting sensors LS1 through LS4 and four light receiving sensors RS1 through RS4 are shown in FIG. 4.

A plasma chamber 50 is symmetrically provided with a first plurality of transparent windows A1 through A8 and an opposing second plurality of transparent windows B1 through B8. A plurality of light emitting devices LS1 through LS8 is installed on the first plurality of transparent windows A1 through A8. In addition, a plurality of light receiving sensors RS1 through RS8 is installed on the second plurality set of transparent windows B1 through B8, respectively. As shown in FIGS. 3 and 4, the plurality of light emitting devices LS1 through LS8 and the plurality of light receiving sensors RS1 through RS8 are mounted on the first and second pluralities of transparent windows A1 through A8 and B1 through B8 in such a manner that the devices and sensors are symmetrically opposite to one another. If less than 6V is detected from any one of the plurality of light receiving sensors RS1 through RS8, controller 20 operates the interlock.

As described above, the present invention monitors the deposition level or level of contamination related to polymer particle on inner walls of a plasma chamber in real time, so as to minimize defectives on wafers caused by the contaminate particles. The present invention is also capable of monitoring the deposition level of polymer particles on the inner walls of the plasma chamber in situ.

While the present invention has been particularly shown and described with reference to exemplary embodiments thereof, it will be understood by those of ordinary skill in the art that various changes in form and details may be made therein without departing from the scope of the present invention as defined by the following claims.

What is claimed is:

1. A system for monitoring particle contaminates in a semiconductor manufacturing device, comprising:
    a process chamber configured to etch or coat a semiconductor wafer;
    at least two transparent windows installed on opposite sides of the process chamber;
    a light emitting device installed on one of the at least two transparent windows;
    a light receiving sensor installed on the other one of the at least two transparent windows;
    a controller detecting a voltage level generated by the light receiving sensor and indicating a level of contamination; and
    an O-ring fitted in an internal boss associated with at least one of the transparent windows and tightly contacting the process chamber, wherein the internal boss is inserted into a groove in the O-ring.

2. A system for monitoring particle contaminates in a semiconductor manufacturing device comprising:
    a process chamber configured to etch or coat a semiconductor wafer;
    at least two transparent windows installed on opposite sides of the process chamber;
    a light emitting device installed on one of the at least two transparent windows;
    a light receiving sensor installed on the other one of the at least two transparent windows;
    a controller detecting a voltage level generated by the light receiving sensor and indicating a level of contamination;
    an alarm generator to generate an alarm if the level of contamination rises above a set level; and
    an O-ring fitted in an internal boss associated with at least one of the transparent windows and tightly contacting the process chamber, wherein the internal boss is inserted into a groove in the O-ring.

3. A system for monitoring particle contaminates in a semiconductor manufacturing device comprising:
    a process chamber configured to etch or coat a semiconductor wafer;
    more than two transparent windows, at least two transparent windows installed on opposite sides of the process chamber;
    a light emitting device installed on one of the at least two transparent windows;
    a light receiving sensor installed on the other one of the at least two transparent windows;
    a controller detecting a voltage level generated by the light receiving sensor and indicating a level of contamination; and
    an O-ring fitted in an internal boss associated with at least one of the transparent windows and tightly contacting the process chamber, wherein the internal boss is inserted into a groove in the O-ring.

4. The system of claim 3, wherein a number of transparent windows is even, and the transparent windows are symmetrically installed opposite one another.

5. The system of claim 3, wherein the at least two transparent windows are quartz.

6. An apparatus for monitoring particle contamination in a process chamber configured to etch or coat a semiconductor wafer, the apparatus comprising:
    first and second transparent windows symmetrically installed on both sides of the processing chamber;
    a light emitter installed on the first transparent window and emitting light towards the second transparent window;
    a light receiving sensor installed on the second transparent window, detecting from the light emitter, and generating a detected voltage in response to the detected light, and
    a controller receiving the detected voltage and comparing the detected voltage to a set voltage and
    an O-ring fitted in an internal boss associated with at least one of the transparent windows and tightly contacting the process chamber, wherein the internal boss is inserted into a groove in the O-ring.

7. The apparatus of claim 6, further comprising a display or an alarm responsive to an interlock signal generated by the controller indicating that the detected voltage is less than the set voltage.

* * * * *